United States Patent [19]

Hennart et al.

[11] 4,439,415

[45] Mar. 27, 1984

[54] DEVICE INTENDED FOR DISPENSING INSECTICIDE VAPORS

[75] Inventors: Claude Hennart, Seraincourt; Jacques Courdent, Lavausseau, both of France

[73] Assignee: Airwick Industries, Inc., Carlstadt, N.J.

[21] Appl. No.: 243,671

[22] Filed: Mar. 13, 1981

[30] Foreign Application Priority Data

Mar. 21, 1980 [LU] Luxembourg .......................... 82279
Oct. 20, 1980 [LU] Luxembourg .......................... 82867

[51] Int. Cl.³ .................... A01N 25/26; A01N 25/34; A01N 37/00; A01N 37/08
[52] U.S. Cl. ....................................... 424/16; 424/21; 424/27; 424/186; 424/306
[58] Field of Search ................. 424/16, 21, 27, 40, 424/306, 186

[56] References Cited

U.S. PATENT DOCUMENTS

| 3,723,615 | 3/1973 | Okuno ................................. 424/40 |
| 3,835,176 | 9/1974 | Matsuo et al. ..................... 424/306 |
| 3,911,101 | 10/1975 | Okuno ................................. 424/40 |
| 3,943,239 | 3/1976 | Yamaguchi et al. ................ 424/27 |
| 3,966,963 | 6/1976 | Okuno et al. ....................... 424/40 |
| 4,296,091 | 10/1981 | Joly et al. ........................... 424/16 |

FOREIGN PATENT DOCUMENTS 1197301  1/1959  France .
1596401  7/1970  France .
1602397  12/1970  France .

*Primary Examiner*—Douglas W. Robinson
*Attorney, Agent, or Firm*—Harry Falber

[57] ABSTRACT

Device which is intended for dispensing insecticide vapors and which can be used in or on a heating apparatus, the said device consisting of several different juxtaposed solid compositions each containing a substance with an action against insects, which is absorbed in an absorptive bulk material, the said active substance being chosen, in at least one of the compositions, from the group comprising the pyrethrinoids and the isopyrethrinoids.

6 Claims, No Drawings

DEVICE INTENDED FOR DISPENSING INSECTICIDE VAPORS

The present invention relates to formulation devices which can be used in or on a heating apparatus and which are intended for dispensing insecticide vapours.

It is known to use heat in order to evaporate insecticidal substances into the atmosphere, either by the combustion of a hydrocarbon gas (British Pat. No. 1,366,041), or by means of an electric bulb (French Pat. Nos. 921,852 and 986,269), or by means of an electrical apparatus known especially for this use (British Pat. Nos. 1,379,782, 1,429,032 and 2,003,034; Spanish Pat. No. 245,083; French Pat. Nos. 1,092,141, 1,165,348 and 2,054,435; and Italian Pat. No. 713,459).

The systems suitable for this purpose use solid compositions containing one or more active substances impregnating an absorptive bulk material; compositions of this type are described in the abovementioned patents and in various other patents (French Pat. No. 2,201,832; and Japanese application Nos. 54/092,620, 73/77,020, 74/66,823 and 76/133,426).

These compositions generally comprise only one active substance. Now, it is frequently advantageous to combine the action of several active substances because they can mutually enhance their action or have different actions and can thus form a combination possessing a broader spectrum of effectiveness, as can be seen, for example, in U.S. Pat. No. 3,934,023 or in Japanese patent application No. 77/039,890.

If it is necessary to combine several active substances, it quite naturally comes to mind to bring them together in one and the same composition. Now, the Applicant Company has discovered that the effectiveness of the combinations of active substances is much greater if these active substances are distributed separately and in a juxtaposed manner in the absorptive materials, rather than as a mixture.

The invention thus relates to a device which is intended for dispensing insecticide vapours and which can be used in or on a heating apparatus, the said device consisting of several different juxtaposed solid compositions each containing a substance with an action against insects, which is absorbed in an absorptive bulk material, the said active substance being chosen, in at least one of the compositions, from the group comprising the pyrethrinoids and the isopyrethrinoids.

If appropriate, one or more of the said compositions can also contain an inert adjuvant chosen from the group comprising diluents, thickeners, perfumes, synergistic agents, dyestuffs, stabilisers, insect lures and insect repellants.

If all the compositions do not each contain an active substance chosen from the group comprising the pyrethrinoids and the isopyrethrinoids, the active substance can be chosen, for example, from the group comprising synergistic agents, insect repellants, insect lures and the known insecticidal compounds other than the pyrethrinoids and the isopyrethrinoids.

An insecticidal compound other than a pyrethrinoid or isopyrethrinoid can be, for example, an organochlorine compound having a vapour pressure of more than $1.10^{-6}$ mm Hg at 25° C. or an organophosphorus compound having a vapour pressure of more than $5.10^{-5}$ mm Hg at 25° C.

Non-limiting examples of suitable organochlorine compounds are hexachlorocyclohexane and its isomer known under the name lindane, chlordane and heptachlor.

Non-limiting examples of suitable organophosphorus compounds are dichlorvos, carbophenothion methyl, trichlormetafos-3, fenchlorphos, demethion, phorate, demetonmethyl, naled or dibrom, chlorothion, thiometon, demeton, chlormephos, pirofos, acetofos-methyl, bromophos, dichlorfenthion, acetofos, mevinphos and, more generally, the compounds mentioned in French Pat. No. 2,292,430.

The pyrethrinoids which can be used as the active substance include, in particular, the esters formed between a cyclopropanecarboxylic acid, such as 2,2,3,3-tetramethylcyclopropanecarboxylic acid or chrysanthemic acid or 3-(2,2-butano- or 2,2-dibromo- or 2,2-dichloro- or 2,2-difluoro-vinyl)-2,2-dimethylcyclopropanecarboxylic acids, in their racemic or resolved forms (d and/or l, cis and/or trans), and the following alcohols: 3-ethyl-2-methyl-4-oxocyclopent-2-enol, 3-allyl-2-methyl-4-oxocyclopent-2-enol, 3-methallyl-2-methyl-4-oxocyclopent-2-enol, 3-crotyl-2-methyl-4-oxocyclopent-2-enol, 3-(3-methylprop-2-enyl)-2-methyl-4-oxocyclopent-2-enol, 3-(2-chloroallyl)-2-methyl-4-oxocyclopent-2-enol, 3-(3-chloroallyl)-2-methyl-4-oxocyclopent-2-enol, 3-furfuryl-2-methyl-4-oxocyclopent-2-enol, 1-phenylprop-2-ynol, 1-(3-chlorophenyl)-prop-2-ynol, 1-(3-fluorophenyl)-prop-2-ynol, 1-(3-trifluoromethylphenyl)-prop-2-ynol, 1-(thien-2-yl)-prop-2-ynol, 1-(furan-2-yl)-prop-2-ynol, 4-phenylbut-2-enol, 4-(3-methylphenyl)-but-2-enol, 4-(2-methylphenyl)-but-2-enol, 4-(2,3-dimethylphenyl)-but-2-enol, 4-(2-methoxyphenyl)-but-2-enol, 4-(2-chlorophenyl)-but-2-enol, 4-(3-chlorophenyl)-but-2-enol, 4-(2,3-dichlorophenyl)-but-2-enol, 4-(3-bromophenyl)-but-2-enol, 4-phenylbut-2-ynol, 4-(furan-2-yl)-but-2-ynol, 4-(thien-2-yl)-but-2-ynol, 5-methylhex-5-en-2-ynol, 5-methylhexa-2,5-dienol, 5,6-dimethylhept-5-en-2-ynol, 2-methylbenzyl alcohol, 3-methylbenzyl alcohol, 4-methylbenzyl alcohol, 2,3-dimethylbenzyl alcohol, 2,4-dimethylbenzyl alcohol, 2,5-dimethylbenzyl alcohol, 2,6-dimethylbenzyl alcohol, 3,4-dimethylbenzyl alcohol, 3,5-dimethylbenzyl alcohol, 2,4,6-trimethylbenzyl alcohol, 4-allylbenzyl alcohol, 4-allyl-2,6-dimethylbenzyl alcohol, 4-methallylbenzyl alcohol, 4-(but-3-enyl)-benzyl alcohol, 4-vinylbenzyl alcohol, 4-cyanobenzyl alcohol, 4-trifluoromethylbenzyl alcohol, 4-nitrobenzyl alcohol, 3-methylfurfuryl alcohol, 5-methylfurfuryl alcohol, 3,5-dimethylfurfuryl alcohol, 4,5-dimethylfurfuryl alcohol, 5-allylfurfuryl alcohol, 5-propargylfurfuryl alcohol, (2-methylfuran-3-yl)-methyl alcohol, (2,5-dimethylfuran-3-yl)-methyl alcohol, (2,4,5-trimethylfuran-3-yl)-methyl alcohol, (5-allylfuran-3-yl)-methyl alcohol, (5-allyl-2-methylfuran-3-yl)-methyl alcohol, (2-methyl-5-propargylfuran-3-yl)-methyl alcohol, tetrahydrophthalimidomethanol, (5-benzylfuran-3-yl)-methanol, (5-alpha-cyanobenzylfuran-3-yl)-methanol, (5-alpha-ethynylbenzylfuran-3-yl)-methanol, 3-phenoxy-alpha-cyanobenzyl alcohol and 3-phenoxy-alpha-ethynylbenzyl alcohol.

These esters include, in particular, the substances known under the names allethrin, bioallethrin, S-bioallethrin, cinerin, furethrin, dimethrin, benathrin, kadethrin, prothrin (or furamethrin), proparthrin, tetramethrin, resmethrin, bioresmethrin, phenothrin, d-phenothrin, permethrin, biopermethrin, cypermethrin, bromethrin, decamethrin and fluorethrin.

The isopyrethrinoids suitable as the active substance consist of the esters formed between the above-mentioned alcohols and the acids, in their racemic or optically active form, defined by the formula

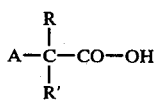

in which R is a lower alkyl, lower alkenyl or cyclopropyl radical, R' being a hydrogen atom, or alternatively R and R' together are a divalent 1,3-propano radical; and A is an aromatic nucleus, chosen from the group comprising benzene, furan, pyrrole and thiophene, which can carry one or two substituents chosen from the group comprising bromine, chlorine, fluorine, and alkyl and alkoxy radicals containing one to four carbon atoms, or alternatively A is a naphthyl radical or a 3,3-dibromoprop-2-enyl or 3,3-dichloroprop-2-enyl radical or an alkyl radical containing one to ten carbon atoms.

The acids defined in this way include the following in particular: 2-phenylisovaleric, 2-phenylisocaproic, 2-cyclopropyl-2-phenylacetic, 2-(4-chlorophenyl)-propionic, 2-(4-chlorophenyl)-butyric, 2-(4-chlorophenyl)-isovaleric, 2-(4-chlorophenyl)-isocaproic, 2-(4-chlorophenyl)-3,3-dimethylbutyric, 2-(4-chlorophenyl)-but-3-enoic, 2-(4-chlorophenyl)-pent-4-enoic, 2-cyclopropyl-2-(4-chlorophenyl)-acetic, 1-phenylcyclobutanecarboxylic, 1-(4-chlorophenyl)-cyclobutanecarboxylic, 2-(4-fluorophenyl)-isovaleric, 2-(4-bromophenyl)-isovaleric, 2-(2,4-dichlorophenyl)-isovaleric, 2-(4-methylphenyl)-isovaleric, 2-(4-methoxyphenyl)-isovaleric, 2-(4-chloro-2-methylphenyl)-isovaleric, 2-(furan-2-yl)-isovaleric, 2-(thien-2-yl)-isovaleric, 2-cyclopropyl-2-(furan-2-yl)-acetic, 2-cyclopropyl-2-(thien-2-yl)-acetic, 2-(naphth-2-yl)-isovaleric, 2-cyclopropyl-2-(naphth-2-yl)-acetic, 5,5-dichloro-2-isopropylpent-4-enoic, 5,5-dibromo-2-isopropylpent-4-enoic, 5,5-dichloro-2-cyclopropylpent-4-enoic, 5,5-dibromo-2-cyclopropylpent-4-enoic, 5,5-dichloro-2-tert.-butylpent-4-enoic, 2-(pyrrol-1-yl)-isovaleric, 2-isopropylisovaleric, 2-isopropyl-n-valeric, 2-isopropylhexanoic, 2-isopropyloctanoic, 2-isopropyldecanoic, 2-isopropyldodecanoic, 2-ethyl-n-valeric, 2-ethyloctanoic, 2-ethyldecanoic and 2,2-diethyldecanoic acids.

Such acids and their esters are described, in particular, in German Pat. Nos. 2,727,323, 2,750,169, 2,753,605, 2,810,031 and 2,925,337, in U.S. Pat. No. 4,164,415, in Belgian Pat. Nos. 853,411, 855,518, 857,248, 857,859, 860,687 and 862,133, in British Pat. No. 1,514,557, in European Pat. Nos. 6,630, 7,421 and 9,637, in French Pat. Nos. 2,359,813, 2,372,799 and 2,376,118 and in Japanese patent application Nos. 52/153,951, 53/059,646, 53/108,954, 54/144,332, 55/009,049 and 55/028,942.

The isopyrethrinoids formed in this way include, in particular, the substances known under the names fenpropanate and fenvalerate.

The synergistic agents, when at least one is present in one of the compositions, are chosen from the group comprising the benzodioxoles, the polychlorinated ethers and the N-alkyl-norborn-5-ene-2,3-dicarboximides.

Examples of suitable benzodioxoles are safrole, isosafrole, 5-cyanobenzo-1,3-dioxole, 5-ethynylbenzo-1,3-dioxole, 5-hydroxymethylbenzo-1,3-dioxole, 5-cyanomethylbenzo-1,3-dioxole, 5,6-dichlorobenzo-1,3-dioxole, 5-chloro-6-cyanobenzo-1,3-dioxole, 5-bromo-6-cyanobenzo-1,3-dioxole, 5-chloro-6-cyanomethylbenzo-1,3-dioxole, 5-chloro-6-hydroxybenzo-1,3-dioxole, 5-chloro-6-hydroxymethylbenzo-1,3-dioxole and 5-chloro-6-ethynylbenzo-1,3-dioxole.

Examples of suitable polychlorinated ethers are 1,1,1,2,6,7,7,7-octachloro-4-oxaheptane and 1,1,2,6,7,7-hexachloro-4-oxahepta-1,6-diene.

Examples of suitable N-alkyl-norborn-5-ene-2,3-dicarboximides are those in which the alkyl radical is an isobutyl, sec.-butyl, tert.-butyl, isopentyl, 2-methylbutyl, isohexyl, 2-methylhexyl, 2-ethylbutyl or isodecyl radical.

The insect lures, when at least one is present in one of the compositions, are chosen from the group comprising all the ones known to those skilled in the art, for example fruit aromas, caramel, cheese and meat aromas, aminoacids, pollen extracts, thymol, skatole, indole, eugenol, paraformaldehyde, hexamethylenetetramine, ammonium carbamate, aliphatic amines, papain, pancreatin, aliphatic acids, vanillin, 3-chloro-3-methylbut-1-ene, 1-chloro-3-methylbut-2-ene and higher alkenes containing 20 to 27 carbon atoms, such as (cis)-tricos-9-ene.

The insect repellants, when at least one is present in one of the compositions, are, for example, the dialkyl succinates, maleates and fumarates, the alkyl mandelates, the N,N-dialkyl-benzamides and -toluamides, the cyclopropanecarbonamides, the 1-alkanoyl[a]hexahydrobenzofurans, the 3,6-dioxadecyl alkanoates, citronellal and its dialkylacetals, and the alkylhexanediols.

The diluents, when at least one is present in one of the compositions, are chosen from the group comprising liquid or solid organic compounds which have a solvent power with respect to the insecticidal compound. The diluents used preferably have a vapour pressure which is at least equal to that of the active substance which accompanies it; even more preferably, this vapour pressure is greater than that of the active substance.

Suitable diluents include, in particular, those chosen from the group comprising the following chemical families:

(1) the monoesters formed between alkanols and hydrocarbon monocarboxylic acids, for example the alkyl acetates, such as those in which alkyl is hexadecyl or octadecyl, the alkyl butyrates and isobutyrates, such as those in which alkyl is dodecyl, tetradecyl, hexadecyl or octadecyl, the alkyl hexanoates, the alkyl octanoates, the alkyl decanoates, the alkyl laurates, undecanoates, undecenoates and myristates, such as those in which alkyl is hexyl, octyl, decyl or dodecyl, the alkyl palmitates, oleates and stearates, such as those in which alkyl is propyl, butyl, isobutyl, amyl, hexyl or octyl, and the alkyl benzoates, phenylacetates and phenylpropionates, such as those in which alkyl is hexyl, octyl, decyl or dodecyl;

(2) the diesters formed between alkanols and hydrocarbon dicarboxylic acids, for example the dialkyl adipates, such as dioctyl adipate, dinonyl adipate, didecyl adipate and didodecyl adipate, the dialkyl sebacates, such as dibutyl sebacate, dipentyl sebacate, dioctyl sebacate and didecyl sebacate, the dialkyl azelates, such as dioctyl azelate and didecyl azelate, and the dialkyl phthalates, such as dibutyl phthalate, dioctyl phthalate, didecyl phthalate, bis-(undecyl) phthalate, bis-(dodecyl) phthalate, bis-(tridecyl) phthalate, bis-(tetradecyl) phthalate and dicetyl phthalate;

(3) the diesters formed between unsubstituted or alkyl-substituted phenols and hydrocarbon dicarboxylic acids, for example the diaryl phthalates, such as diphenyl phthalate and the dicresyl phthalates;

(4) the diesters formed between unsubstituted or alkyl-substituted cycloalkanols and hydrocarbon dicarboxylic acids, for example dicyclohexyl phthalate, the bis(methylcyclohexyl) phthalates, the bis-(trimethylcyclohexyl) phthalates and the bis-(tetramethylcyclohexyl) phthalates;

(5) the diesters formed between phenylalkanols and hydrocarbon dicarboxylic acids, for example dibenzyl sebacate, dibenzyl azelate and the bis-(phenylpropyl) sebacates;

(6) the diesters formed between alkanediols and hydrocarbon monocarboxylic acids, for example 2,2,4-trimethylpentane-1,3-diol diisobutyrate;

(7) the triesters formed between unsubstituted or alkyl-substituted phenols and phosphoric acid, for example triphenyl phosphate, tris-(4-tert.-butylphenyl) phosphate and the tricresyl phosphates;

(8) the triesters formed between alkanols and phosphoric acid, for example trioctyl phosphate, tridecyl phosphate and tridodecyl phosphate;

(9) polyalkylene glycols, for example the polyethylene glycols and the polypropylene glycols;

(10) fatty alcohols, for example hexadecanol, octadecanol and octadec-9-enol;

(11) fatty acids, for example lauric, myristic, palmitic, stearic and oleic acids;

(12) alkanes containing at least 18 carbon atoms, for example octadecane, eicosane, docosane and tetracosane, and their mixtures known under the names vaseline oil, paraffin oil, heavy oil, gas oil, fuel oil, road oil, valve oil, mazut, vaseline, petroleum, crude paraffin, paraffin, microcrystalline wax, ozokerite and ceresin;

(13) alkanones containing at least eighteen carbon atoms, for example caprinone, laurone, myristone, palmitone and stearone; and

(14) alkenones containing at least eighteen carbon atoms, for example heneicosa-1,20-dien-11-one and oleone.

Examples of thickeners are metal salts of fatty acids, such as the aluminium or magnesium mono-, di- and tri-stearates, or amine salts of fatty acids, such as the hexadecylaminopropylene-amine, octadecylaminopropylene-amine or octadecenylaminopropylene-amine dioleates, or the modified montmorillonites, such as the ammonium salts of dimethyl di-(higher alkyl)-bentonite.

The stabilisers, when at least one is present in one of the compositions, are chosen from the group comprising all the ones known to those skilled in the art, for example phenolic compounds, such as resorcinol, pyrogallol, hydroquinone, 2-tert.-butyl-4-methoxyphenol and 2,6-di-tert.-butyl-4-methylphenol, bis-phenol compounds, such as the bis-(hydroxyphenyl)-ethanes, bis-(hydroxyphenyl)-methanes and bis-(hydroxyphenyl)-propanes, bis-(3-tert.-butyl-5-ethyl-2-hydroxyphenyl)-methane and bis-(3-tert.-butyl-4-hydroxyphenyl)-methane, and the O,O-dialkyl (hydroxybenzyl)-phosphonates, such as O,O-diethyl-(4-hydroxy-3,5-di-tert.-butylbenzyl)-phosphonate.

The absorptive bulk materials can be chosen from the group comprising cellulosic papers and cardboards composed of wood fibres, cereal fibres, alfa fibres, cotton fibres or scrap paper, and materials composed of asbestos fibres, glass fibres, wool fibres and/or polymeric fibres, and from the group comprising baked clays, sintered aluminas and biscuit porcelains.

The substance constituting the bulk material can also contain fillers chosen from the group comprising organic powders, mineral powders, pigments, dyestuffs and binders.

The bulk materials can adopt any of the known forms, such as plates and blocks.

The plates can be round, oval, square, rectangular or triangular or can have any other polygonal shape, it being possible for their total surface area to be either as little as a few square centimeters or several square decimeters, and for their thickness to vary from 0.1 to 6 millimeters.

The blocks can be cubic, prismatic, cylindrical, or of elliptical section or can have any other polyhedral shape, it being possible for their total surface area to vary from as little as a few square centimeters to several square decimeters.

A solid composition according to the invention is obtained by impregnating the absorptive bulk material with the liquid mixture of the other constituents of the composition (active substance and, if appropriate, adjuvants). The impregnation can be carried out by pouring the liquid mixture onto the absorptive material or by soaking the latter in the liquid, the soaking being followed by draining, if appropriate; this operation can be mechanised by using, for example, a metering pump or a row of sprinklers with a constant output; it is also possible to employ an adjustable-pressure squeezing roller so as to make it possible to retain the desired proportion of liquid; an adjustable-speed centrifuge can also be used for the same purpose. An impregnation method of industrial value consists, for example, in the use of long strips impregnated in a continuous process and subsequently cut to the desired dimensions. The impregnation can also be carried out by subjecting the absorptive material to a vacuum, in the presence of the liquid mixture.

The impregnation can also be carried out automatically by means of a machine comprising one or more injection syringes and a conveyor belt on which the absorptive materials to be impregnated are passed under the said syringes. It is also possible to use a solution of the liquid mixture in a volatile solvent, the latter subsequently being evaporated off.

There are preferably two or three solid compositions constituting the device. They can be simply placed near one another without a physical means of connection, or, on the other hand, they can constitute a single unit.

If the device is a single unit, the solid compositions can be joined by any known means, such as an adhesive, a cement or a system of fasteners, nails, mounts or metal or plastic crimps.

The device can also consist of only one absorptive bulk material into which the chosen active ingredients, accompanied, if appropriate, by an inert adjuvant, have been absorbed separately and each in a different zone. In this case, it is possible to leave one zone of the bulk material unimpregnated, so as to constitute a means of separation between the active ingredients; it is also possible to create an impenetrable barrier in this zone by means of pre-impregnation with a substance, the purpose of which is to render the conventional material non-absorptive.

A barrier can thus be formed, for example by means of a vegetable, animal or paraffin wax deposited in the liquid state at the point where the barrier is to be produced; the wax is absorbed in the liquid state and, after cooling, forms an impassable means of separation between the active ingredients.

Another substance which can be used to produce a barrier consists, for example, of an alkali metal silicate in aqueous solution, the solution being concentrated and then dried.

Likewise, it is possible to use a solution of natural or synthetic resin in a volatile solvent, the latter being subsequently removed by drying.

A particularly advantageous process consists in creating the barrier in situ by using a polymerisable substance chosen from the group comprising monomers, prepolymers and combinations of compounds which are capable of reacting with one another to give polymeric resins.

Valuable monomers are, in particular, styrene, methyl acrylate, ethyl acrylate, dimethyl, diethyl, dipropyl and dibutyl maleates and cyanoacrylic acid esters.

The prepolymers are chosen, for example, from the group comprising polyesters, such as those formed between dicarboxylic acids, such as adipic, sebacic, azelaic, maleic, phthalic or tetrahydrophthalic acid, and polyols, such as ethylene glycol and propylene glycol, polyethylene glycol and polypropylene glycol, glycerol and pentaerythritol.

If a monomer or a prepolymer is used, an accelerator and/or a polymerisation catalyst can advantageously be added thereto at the moment of the treatment of the absorptive bulk material, or, preferably, this accelerator and/or catalyst can be introduced separately into the treated zone before, during or after the treatment.

The accelerators are, in particular, cobalt salts or vanadium salts and dialkylanilines; polymerisation catalysts are, in particular, percarboxylic acids, their esters and their salts, and acyl peroxides, alkyl peroxides, cumene peroxide or ketone peroxides.

To promote the polymerisation, it is also possible to carry out the reaction at a temperature above ambient temperature, for example at between 40° and 80° C., during the treatment, or to subject the treated zone to this temperature after the treatment. It is also possible to subject the treated zone to infra-red radiation, ultraviolet radiation, ultrasound, microwaves or gamma rays.

Of course, combinations of several prepolymers or of a prepolymer (or prepolymers) and a monomer (or monomers) can be used in order to impart particular characteristics to the polymers formed.

Combinations of compounds which are capable of reacting with one another are, in particular, those leading to the formation of resins of the epoxy, epoxy/ester and epoxy/phenol type, those leading to the formation of amino-resins, such as the urea/formaldehyde or melamine/formaldehyde resins, and those leading to the formation of polyurethane resins.

These compounds can be mixed just before application to the absorptive bulk material; it is also possible to deposit each of the compounds, at the same time or successively, onto the said material, so as to permit mixing to take place in situ.

The devices according to the invention exhibit the advantage, for equal amounts of substances and under the same heating conditions, of providing insecticide vapours which are more effective than those dispensed by the known devices, in which the active substances used are mixed to form a single composition.

One characteristic of the devices according to the invention is that they make it possible to choose, for each of the solid compositions, a surface area of evaporation which is related to the active substance present, and hence separately to adjust the amount of each of the active substances evaporated.

Another characteristic of the devices according to the invention is that they make it possible, by using a suitable heating apparatus, to heat each of the solid compositions to a different temperature which is related to the active substance present, and hence, in this case also, separately to adjust the amount of each of the active substances evaporated.

The advantage of the devices according to the invention is illustrated by the following experiments.

Experiment 1

Two devices, 1-A and 1-B, having the same total surface area and using the same absorptive bulk material, were prepared. The device 1-A consisted of two different compositions, 1-A' and 1-A", juxtaposed and joined by metal fasteners; the device 1-B consisted of only one homogeneous composition containing all the constituents of the compositions 1-A' and 1-A". These devices are specified in detail below:

|  | 1-A | | 1-B |
| --- | --- | --- | --- |
|  | 1-A' | 1-A" |  |
| Allethrin | 50 mg | — | 50 mg |
| Tetramethrin | — | 50 mg | 50 mg |
| Dioctyl sebacate | 75 mg | — | 75 mg |
| Stabiliser[a] | — | 20 mg | 20 mg |
| Cellulose | 880 mg | 1,760 mg | 2,640 mg |
| Surface area | 714 mm$^2$ | 1,428 mm$^2$ | 2,142 mm$^2$ |
| Length | 34 mm | 42 mm | 63 mm |
| Width | 21 mm | 34 mm | 34 mm |
| Thickness | 3 mm | 3 mm | 3 mm |

[a]O,O—Diethyl (4-hydroxy-3,5-di-tert.-butylbenzyl)-phosphonate.

The devices prepared in this way were each placed on the appropriate part of an electrical apparatus having a heated surface area of 35×64 mm and a 225 volt alternating current supply so as to a reach a temperature of 200° C.

The apparatuses equipped in this way with their device were each placed in a 28 m$^3$ room kept at 25° C., and 100 domestic flies were released into the room.

After 45 minutes, the number of dead flies or flies in the dorsal decubitus position was counted in each of the rooms.

The result of these counts was as follows:
 1-A: 65
 1-B: 43

Experiment 2

The procedure of Experiment 1 was followed, the devices 2-A and 2-B being prepared; the device 2-A was composed of two different compositions, 2-A' and 2-A", obtained by impregnating each of the two parts of a cellulosic carboard, the said parts being separated by an impregnated line of a polyester prepolymer catalysed by a peroxide; the device 2-B consisted of only one homogeneous composition containing all the constituents of the compositions 2-A' and 2-A". These devices are specified in detail below:

|  | 2-A | | 2-B |
| --- | --- | --- | --- |
|  | 2-A' | 2-A" |  |
| Bioallethrin | 40 mg | — | 40 |
| d-Phenothrin | — | 60 mg | 60 mg |

-continued

| | 2-A | | |
| --- | --- | --- | --- |
| | 2-A' | 2-A" | 2-B |
| Butyl stearate | 40 mg | — | 40 mg |
| Cellulose | 880 mg | 1,760 mg | 2,640 mg |
| Surface area | 646 mm² | 1,394 mm² | 2,040 mm² |
| Length | 34 mm | 41 mm | 60 mm |
| Width | 19 mm | 34 mm | 34 mm |
| Thickness | 3 mm | 3 mm | 3 mm |

The devices prepared in this way were each placed on the appropriate part of an electrical apparatus having a heated surface area of 35×64 mm and a 225 volt alternating current supply so as to reach a temperature of 160° C.

The apparatuses equipped in this way with their device were each placed in a 28 m³ room kept at 25° C., and 100 domestic flies were released into the room.

After 30 minutes, the number of dead flies or flies in the dorsal decubitus position was counted in each of the rooms. The result of these counts was as follows:

2-A: 38
2-B: 21

The results of these experiments show that the insecticidal effectiveness of a device in which the compositions are separated is greater than that of a known device containing the same constituents in the same proportions, but in a single composition.

Experiment 3

Two devices, 3-A and 3-B, having the same total surface area and using the same absorptive bulk material, were prepared. The device 3-A consisted of two different compositions, 3-A' and 3-A", obtained by impregnating each of the two parts of a cellulosic cardboard, the said parts being separated by an impregnated line consisting of a styrene/propylene glycol maleate-phthalate copolymer; the device 3-B consisted of only one homogeneous composition containing both the compositions 3-A' and 3-A". These devices are specified in detail below:

| | 3-A | | |
| --- | --- | --- | --- |
| | 3-A' | 3-A" | 3-B |
| d-Allethrin | — | 30 mg | 30 mg |
| d-Phenothrin | 10 mg | — | 10 mg |
| Isobutyl stearate | — | 12.5 mg | 12.5 mg |
| Stabiliser (a) | 1 mg | 3 mg | 4 mg |
| Cellulose | 400 mg | 567 mg | 967 mg |
| Surface area | 720 mm² | 1,020 mm² | 1,740 mm² |
| Length | 24 mm | 34 mm | 58 mm |
| Width | 30 mm | 30 mm | 30 mm |
| Thickness | 1.25 mm | 1.25 mm | 1.25 mm |

The devices prepared in this way were each placed on the appropriate part of an electrical apparatus having a surface area of 30×60 mm, heated by a 225 volt alternating current so as to reach a temperature of 165° C.

The apparatuses equipped in this way with their device were each placed in a 28 m³ room kept at 25° C. and subjected to a continuous air flow of 500 m³/hour.

One hundred flies were released into each room at the start of the experiment and then after one hour, and a further ten flies were subsequently added every hour.

Every quarter of an hour during the first hour, and then every hour, the number of dead flies or flies in the dorsal decubitus position was counted in each room and this number was used to calculate the number of flies still alive and troublesome.

The results of these measurements are summarised in the table below.

| Time | 3-A | 3-B |
| --- | --- | --- |
| 15 minutes | 95 | 97 |
| 30 minutes | 73 | 86 |
| 45 minutes | 48 | 72 |
| 1 hour | 31 | 59 |
| 2 hours | 23 | 56 |
| 3 hours | 19 | 62 |
| 4 hours | 16 | 69 |
| 5 hours | 23 | 76 |
| 6 hours | 27 | 83 |
| 7 hours | 35 | 89 |
| 8 hours | 41 | 95 |
| 9 hours | 47 | 102 |

Experiment 4

The procedure of Experiment 3 was followed, using devices 4-A and 4-B consisting of the compositions below, and the rooms in which the apparatuses were placed were subjected to an airflow of 1,000 m³/hour.

| | 4-A | | |
| --- | --- | --- | --- |
| | 4-A' | 4-A" | 4-B |
| Tetramethrin | 30 mg | — | 30 mg |
| d-Phenothrin | — | 20 mg | 20 mg |
| Isobutyl stearate | 30 mg | — | 30 mg |
| Stabiliser (a) | 3 mg | 2 mg | 5 mg |
| Cellulose | 480 mg | 480 mg | 960 mg |
| Surface area | 870 mm² | 870 mm² | 1,740 mm² |
| Length | 29 mm | 29 mm | 58 mm |
| Width | 30 mm | 30 mm | 30 mm |
| Thickness | 1.25 mm | 1.25 mm | 1.25 mm |

The results of the measurements, expressed as the number of live flies, are summarised in the table below:

| Time | 4-A | 4-B |
| --- | --- | --- |
| 15 minutes | 96 | 100 |
| 30 minutes | 90 | 100 |
| 45 minutes | 82 | 98 |
| 1 hour | 74 | 95 |
| 2 hours | 55 | 88 |
| 3 hours | 43 | 76 |
| 4 hours | 35 | 65 |
| 5 hours | 29 | 55 |

What is claimed is:

1. A device for dispensing insecticidal vapors which comprises a cellulosic absorptive substrate having two different pyrethrinoids absorbed into separate sections thereof, said pyrethrinoids being selected from the group consisting of allethrin, bioallethrin, tetramethrin, d-phenothrin and d-allethrin and being present in weight ratios relative one to the other ranging from 1:1 to 3:1.

2. The system according to claim 1, wherein the absorptive substrate has a thickness of between 0.1 and 6 millimeters.

3. The system according to claim 1, wherein the different impregnated areas are separated by an area containing insecticide.

4. The system according to claim 3, wherein the area not containing insecticide is impregnated with a surface sealing substance.

5. The system according to claim 4, wherein said substance is selected from the group consisting of waxes, alkali metal silicates, natural resins and synthetic polymeric resins.

6. The system according to claim 5, wherein the polymerisable material utilized in said polymeric resin is a monomer selected from the group consisting of styrene, acrylic acid esters, maleic acid esters and cyanoacrylic acid esters.

* * * * *